United States Patent [19]

Hahn et al.

[11] Patent Number: 5,240,566
[45] Date of Patent: Aug. 31, 1993

[54] SEPARATION PROCESS

[75] Inventors: Bruce R. Hahn, Hudson; Thomas R. Maier, Brecksville; Surendra K. Chawla, Copley, all of Ohio

[73] Assignee: The Goodyear Tire & Rubber Company, Akron, Ohio

[21] Appl. No.: 986,201

[22] Filed: Dec. 7, 1992

[51] Int. Cl.$^5$ .......................... B01D 3/14; B01D 3/34
[52] U.S. Cl. ........................................ 203/35; 203/12; 203/79; 203/80; 203/85; 562/605; 568/411
[58] Field of Search .................. 203/12, 35, 79, 80, 203/85, DIG. 6; 568/410, 411; 562/605, 608; 585/800; 570/262

[56] References Cited

U.S. PATENT DOCUMENTS

| | | | |
|---|---|---|---|
| 2,381,032 | 8/1945 | Bludworth et al. | 203/35 |
| 4,213,832 | 7/1980 | Zudkevitch et al. | 568/411 |
| 4,609,497 | 9/1986 | Cope | 562/605 |
| 4,730,082 | 3/1988 | Amiet | 203/DIG. 6 |
| 4,879,407 | 11/1989 | Amiet | 203/DIG. 6 |

*Primary Examiner*—Virginia Manoharan
*Attorney, Agent, or Firm*—Alvin T. Rockhill

[57] ABSTRACT

A process for separating acetone, dichloromethane and trifluoroacetic acid from a mixture of acetone, dichloromethane, and a trifluoroacetic acid/acetone azeotrope by (1) fractionally distilling the mixture of acetone, dichloromethane, and the trifluoroacetic acid/acetone azeotrope;

(2) fractionally distilling the mixture of the trifluoroacetic acid/acetone azeotrope and free acetone;

(3) adding at least about 16 parts of water to the trifluoroacetic acid/acetone azeotrope per 100 parts by volume of the trifluoroacetic acid/acetone azeotrope;

(4) fractionally distilling the mixture of free acetone and the water/trifluoroacetic acid azeotrope;

(5) adding at least about 10 parts of sulfuric acid to the water/trifluoroacetic acid azeotrope per 100 parts by volume of the water/trifluoroacetic acid azeotrope;

(6) fractionally distilling the mixture of trifluoroacetic acid and the water/sulfuric acid complex.

16 Claims, No Drawings

SEPARATION PROCESS

BACKGROUND OF THE INVENTION

U.S. Pat. No. 5,061,425 discloses a process for producing high modulus, high tenacity polyethylene terephthalate (PET) filament by spinning a solution of PET in a mixed solvent system containing trifluoroacetic acid and dichloromethane through a die and into a coagulation medium containing acetone. This results in the formation of a mixture of acetone, trichloroacetic acid, and dichloromethane. U.S. Pat. No. 4,792,573, U.S. Pat. No. 4,917,845, and U.S. Pat. No. 4,957,945 disclose a technique for producing ultra-high molecular weight polyester resin. One of the techniques disclosed in these patents also results in the formation of a mixture of acetone, trichloroacetic acid, and dichloromethane. In commercial operations it is important to be able to recycle such solvent mixtures to make the process commercially and environmentally feasible. In other words, the organic solvents must be used, collected, separated, and re-used in a closed continuous system.

It is unfortunately not an easy task to separate the three organic solvents present in such mixtures. This is because a trifluoroacetic acid/acetone azeotrope forms making quantitative separation by fractional distillation impossible.

SUMMARY OF THE INVENTION

This invention discloses a process for separating acetone, dichloromethane and trifluoroacetic acid from a mixture of acetone, dichloromethane, and a trifluoroacetic acid/acetone azeotrope comprising the steps of:

(1) fractionally distilling the mixture of acetone, dichloromethane, and the trifluoroacetic acid/acetone azeotrope to separate the dichloromethane from a mixture of the trifluoroacetic acid/acetone azeotrope and free acetone;

(2) fractionally distilling the mixture of the trifluoroacetic acid/acetone azeotrope and free acetone to separate the free acetone from the trifluoroacetic acid/acetone azeotrope;

(3) adding at least about 16 parts of water to the trifluoroacetic acid/acetone azeotrope per 100 parts by volume of the trifluoroacetic acid/acetone azeotrope to break the trifluoroacetic acid/acetone azeotrope producing a mixture of free acetone and a water/trifluoroacetic acid azeotrope;

(4) fractionally distilling the mixture of free acetone and the water/trifluoroacetic acid azeotrope to separate the free acetone from the water/trifluoroacetic acid azeotrope;

(5) adding at least about 10 parts of sulfuric acid to the water/trifluoroacetic acid azeotrope per 100 parts by volume of the water/trifluoroacetic acid azeotrope to break the water/trifluoroacetic acid azeotrope producing a mixture of trifluoroacetic acid and a water/sulfuric acid complex;

(6) fractionally distilling the mixture of trifluoroacetic acid and the water/sulfuric acid complex to separate the trifluoroacetic acid from the water/sulfuric acid complex.

DETAILED DESCRIPTION OF THE INVENTION

Mixtures of acetone, dichloromethane, and trifluoroacetic acid are technically comprised of free acetone, free dichloromethane, and a trifluoroacetic acid/acetone azeotrope. There is no free trifluoroacetic acid in such mixtures (all of the trifluoroacetic acid is in the trifluoroacetic acid/acetone azeotrope). In the first step of the process of this invention, the three component mixture is fractionally distilled to recover the dichloromethane. This fractional distillation is typically conducted at a temperature of about 41° C. (the boiling point of dichloromethane). However, this temperature will vary if the fractional distillation is not carried out under atmospheric pressure. For instance, the dichloromethane will boil at a lower temperature at reduced pressures and will boil at higher temperatures under increased pressures. In any case, the dichloromethane is boiled off and recovered in this fractional distillation step. After the acetone has been removed, the remaining components in the solvent mixture are the free acetone and the trifluoroacetic acid/acetone azeotrope.

In the second step of the process, the mixture of trifluoroacetic acid/acetone azeotrope and free acetone remaining after the first step is fractionally distilled to remove and recover the free acetone from the mixture. Since acetone has a boiling point of 56° C., this fractional distillation step will typically be carried out at that temperature under atmospheric pressure. After all of the free acetone has been recovered, only the trifluoroacetic acid/acetone azeotrope remains.

At this point, at least about 16 parts of water is added to the trifluoroacetic acid/acetone azeotrope per 100 parts by volume of the trifluoroacetic acid/acetone azeotrope. The water breaks the trifluoroacetic acid/acetone azeotrope and produces a mixture of free acetone and a water/trifluoroacetic acid azeotrope. This will typically be accomplished by adding from about 16 parts to about 350 parts of water per 100 parts by volume of the trifluoroacetic acid/acetone azeotrope. It is more typical to add from about 16 parts to about 100 parts of water to the trifluoroacetic acid/acetone azeotrope per 100 parts by volume of the azeotrope. It is normally preferred to add from about 16 parts to about 30 parts of water to the trifluoroacetic acid/acetone azeotrope per 100 parts by volume of the azeotrope. It is beneficial to minimize the amount of water added while still using an amount which ensures that the trifluoroacetic acid/acetone azeotrope is completely broken.

The mixture of free acetone and the water/trifluoroacetic acid azeotrope can then be fractionally distilled to recover the free acetone from the mixture. This fractional distillation is, of course, preferably carried out under atmospheric pressure at a temperature of about 56° C. After the free acetone is removed and recovered, only the water/trifluoroacetic acid azeotrope remains.

The water/trifluoroacetic acid azeotrope is broken by the addition of sulfuric acid. This is carried out by adding at least about 10 parts by volume of sulfuric acid to the water/trifluoroacetic acid azeotrope per 100 parts by volume of the water/trifluoroacetic acid azeotrope. Typically, from about 10 parts to about 140 parts of sulfuric acid is added per 100 parts by volume of the water/trifluoroacetic acid azeotrope. Preferably, from about 20 parts to about 70 parts of sulfuric acid will be added to the water/trifluoroacetic acid azeotrope per 100 parts by volume of the azeotrope. It is normally most preferred to add from about 30 parts to about 50 parts of sulfuric acid to the water/trifluoroacetic acid azeotrope per 100 parts by volume of the azeotrope. After the water/trifluoroacetic acid azeotrope is broken by the addition of sulfuric acid, a mixture of free trifluoroacetic acid and a water/sulfuric acid complex is formed.

The free trifluoroacetic acid can then be removed from the mixture of free trifluoroacetic acid and the water/sulfuric acid complex by fractional distillation. This fractional distillation will typically be carried out under atmospheric pressure at a temperature of about 72° C. As explained before, the temperature at which the fractional distillation is carried out will vary under increased or decreased pressures. After the trifluoroacetic acid is removed and recovered by fractional distillation, only the water/sulfuric acid complex remains.

Water can then be removed from the water/sulfuric acid complex by boiling it out or by simply allowing it to evaporate. By utilizing this procedure of water removal, concentrated sulfuric acid can be produced. The concentrated sulfuric acid produced by such a procedure can then be recycled for utilization in breaking the water/trifluoroacetic acid azeotrope in the fifth step of the process of this invention. In utilizing this process, the sulfuric acid, water, trifluoroacetic acid, dichloromethane, and acetone can all be reused as part of a closed, continuous separation procedure.

This invention is illustrated by the following example which is merely for the purpose of illustration and is not to be regarded as limiting the scope of the invention or the manner in which it can be practiced. This working example illustrates the practicality and the operability of the present invention.

EXAMPLE

A solution containing 50 weight percent trifluoroacetic acid and 50 weight percent dichloromethane was prepared. A mixture of acetone, dichloromethane, and a trifluoroacetic acid/acetone azeotrope was then prepared by mixing 100 ml of the trifluoroacetic acid/dichloromethane solution with 500 ml of acetone. The 600 ml of the mixture of acetone, dichloromethane and the trifluoroacetic acid/acetone azeotrope was then heated in a round bottom flask equipped with a small Vigreux column. The mixture was fractionally distilled and at a temperature of about 40° C., a dichloromethane fraction was collected. After all of the dichloromethane had been separated from the mixture, the temperature was allowed to increase to about 56° C. At that point, an acetone fraction was collected. Titrations of the dichloromethane fraction and the acetone fraction collected with a sodium hydroxide (NaOH) solution showed only a trace amount of acid. The 111.5 ml of residue in the pot was found to be 5.01 molar trifluoroacetic acid. This showed that the residue in the pot was a 3/2 by volume trifluoroacetic acid/acetone azeotrope (within experimental error).

At this point 20 ml of water was added to the trifluoroacetic acid/acetone azeotrope in the round bottom flask. The distillation was continued and additional acetone was collected at a temperature of 56° C. The temperature was then increased and a small fraction was collected at a temperature over the range of 70° C. to 78° C. The fraction collected at 56° C. contained only a trace amount of acid and the small fraction collected from 70° C. to 78° C. contained 2.8% trifluoroacetic acid by weight. The pot was then cooled and 40 ml of concentrated sulfuric acid was subsequently added. The flask was then heated to 72° C. and 29 ml of a trifluoroacetic acid fraction was collected. Titration showed this fraction to be virtually pure trifluoroacetic acid.

This example shows that the procedure of this invention can be successfully used for separating acetone, dichloromethane and trifluoroacetic acid from a mixture of acetone, dichloromethane and a trifluoroacetic acid/acetone azeotrope. Very high levels of purity can be realized by utilizing distillation columns having a large number of theoretical plates.

While certain representative embodiments and details have been shown for the purpose of illustrating the subject invention, it will be apparent to those skilled in this art that various changes and modifications can be made therein without departing from the scope of the subject invention.

What is claimed is:

1. A process for separating acetone, dichloromethane and trifluoroacetic acid from a mixture of acetone, dichloromethane, and a trifluoroacetic acid/acetone azeotrope comprising the steps of:
   (1) fractionally distilling the mixture of acetone, dichloromethane, and the trifluoroacetic acid/acetone azeotrope to separate the dichloromethane from a mixture of the trifluoroacetic acid/acetone azeotrope and free acetone;
   (2) fractionally distilling the mixture of the trifluoroacetic acid/acetone azeotrope and free acetone to separate the free acetone from the trifluoroacetic acid/acetone azeotrope;
   (3) adding at least about 16 parts of water to the trifluoroacetic acid/acetone azeotrope per 100 parts by volume of the trifluoroacetic acid/acetone azeotrope to break the trifluoroacetic acid/acetone azeotrope producing a mixture of free acetone and a water/trifluoroacetic acid azeotrope;
   (4) fractionally distilling the mixture of free acetone and the water/trifluoroacetic acid azeotrope to separate the free acetone from the water/trifluoroacetic acid azeotrope;
   (5) adding at least about 10 parts of sulfuric acid to the water/trifluoroacetic acid azeotrope per 100 parts by volume of the water/trifluoroacetic acid azeotrope to break the water/trifluoroacetic acid azeotrope producing a mixture of trifluoroacetic acid and a water/sulfuric acid complex;
   (6) fractionally distilling the mixture of trifluoroacetic acid and the water/sulfuric acid complex to separate the trifluoroacetic acid from the water/sulfuric acid complex.

2. A process as specified in claim 1 wherein the concentration of the sulfuric acid in the water/sulfuric acid complex separated from the trifluoroacetic acid in step (6) is concentrated by removing a portion of the water therefrom to produce a concentrated sulfuric acid solution.

3. A process as specified in claim 2 wherein the concentrated sulfuric acid solution is utilized as the source of the sulfuric acid employed in step (5).

4. A process as specified in claim 2 wherein the water is removed by evaporation.

5. A process as specified in claim 2 wherein the water is removed by boiling.

6. A process as specified in claim 2 wherein the water removed from the water/sulfuric acid complex is utilized as the source of the water employed in step (3).

7. A process as specified in claim 1 wherein from about 10 parts to about 140 parts of sulfuric acid is added in step (5) per 100 parts by volume of the water/trifluoroacetic acid azeotrope.

8. A process as specified in claim 1 wherein from about 20 parts to about 70 parts of sulfuric acid is added in step (5) per 100 parts by volume of the water/trifluoroacetic acid azeotrope.

9. A process as specified in claim 1 wherein from about 30 parts to about 50 parts of sulfuric acid is added in step (5) per 100 parts by volume of the water/trifluoroacetic acid azeotrope.

10. A process as specified in claim 7 wherein from about 16 parts to about 350 parts of water is added in step (3) per 100 parts by volume of the trifluoroacetic acid/acetone azeotrope.

11. A process as specified in claim 8 wherein from about 16 parts to about 100 parts of water is added in step (3) per 100 parts by volume of the trifluoroacetic acid/acetone azeotrope.

12. A process as specified in claim 9 wherein from about 16 parts to about 30 parts of water is added in step (3) per 100 parts by volume of the trifluoroacetic acid/acetone azeotrope.

13. A process as specified in claim 10 wherein the mixture of acetone, dichloromethane, and the trifluoroacetic acid azeotrope is fractionally distilled in step (1) at a temperature of about 41° C.

14. A process as specified in claim 13 wherein the mixture of the trifluoroacetic acid/acetone azeotrope and free acetone is fractionally distilled in step (2) at a temperature of about 56° C.

15. A process as specified in claim 14 wherein the mixture of free acetone and the water/trifluoroacetic acid azeotrope is fractionally distilled in step (4) at a temperature of about 56° C.

16. A process as specified in claim 15 wherein the mixture of trifluoroacetic acid and the water/sulfuric acid complex is fractionally distilled in step (6) at a temperature of about 72° C.

* * * * *